United States Patent
Benndorf et al.

(10) Patent No.: US 10,426,418 B2
(45) Date of Patent: Oct. 1, 2019

(54) PHANTOMS AND METHODS AND KITS USING THE SAME

(71) Applicant: Baylor College of Medicine, Houston, TX (US)

(72) Inventors: Goetz Benndorf, Houston, TX (US); James Ryan Mason, Bellaire, TX (US)

(73) Assignee: Baylor College of Medicine, Houston, TX (US)

( * ) Notice: Subject to any disclaimer, the term of this patent is extended or adjusted under 35 U.S.C. 154(b) by 173 days.

(21) Appl. No.: 15/550,635

(22) PCT Filed: Apr. 25, 2016

(86) PCT No.: PCT/US2016/029237
§ 371 (c)(1),
(2) Date: Aug. 11, 2017

(87) PCT Pub. No.: WO2016/176150
PCT Pub. Date: Nov. 3, 2016

(65) Prior Publication Data
US 2018/0035962 A1    Feb. 8, 2018

Related U.S. Application Data

(60) Provisional application No. 62/152,694, filed on Apr. 26, 2015.

(51) Int. Cl.
*A61B 6/00* (2006.01)
*G01D 18/00* (2006.01)
(Continued)

(52) U.S. Cl.
CPC .............. *A61B 6/487* (2013.01); *A61B 6/481* (2013.01); *A61B 6/504* (2013.01); *A61B 6/583* (2013.01);
(Continued)

(58) Field of Classification Search
CPC ......... A61B 6/487; A61B 6/481; A61B 6/504; A61B 6/583; G01B 33/5635; G01B 33/58; G01D 18/00
See application file for complete search history.

(56) References Cited

U.S. PATENT DOCUMENTS 3,348,319 A    10/1967 Harrison et al.
4,126,789 A    11/1978 Vogl et al.
(Continued)

OTHER PUBLICATIONS

Chida, et al., "Development of a simple QC phantom for evaluating FPD images", European Society of Radiology, Poster No. C-3012, Congress: ECR 2010, Type: Scientific Exhibit—DOI: 10.1594/ecr2010/C-3012—(downloaded Apr. 6, 2016).
(Continued)

*Primary Examiner* — David P Porta
*Assistant Examiner* — Jeremy S Valentiner
(74) *Attorney, Agent, or Firm* — Saul Ewing Arnstein & Lehr LLP; Kathryn Doyle; Brian R. Landry (57) ABSTRACT

One aspect of the invention provides a phantom including a confined fluidic path defining a plurality of regions of monotonically decreasing, discrete cross-sectional dimensions with respect to an imaging plane. Another aspect of the invention provides a method of assessing imaging. The method includes: placing a phantom as described herein within an imaging system; flowing one or more fluids through the phantom; and capturing one or more images of the phantom. Another aspect of the invention provides a kit for assessing imaging. The kit includes a phantom as described herein and instructions for use.

17 Claims, 10 Drawing Sheets

(51) Int. Cl.
  *G01R 33/48* (2006.01)
  *G01R 33/563* (2006.01)
  *G01R 33/58* (2006.01)

(52) U.S. Cl.
  CPC ......... *G01R 33/5635* (2013.01); *G01R 33/58* (2013.01); *G01D 18/00* (2013.01); *G01R 33/48* (2013.01)

(56) References Cited

U.S. PATENT DOCUMENTS

| | | | | |
|---|---|---|---|---|
| 4,873,707 | A * | 10/1989 | Robertson | A61B 6/583 378/18 |
| 2002/0003854 | A1 * | 1/2002 | Ivan | A61B 6/4441 378/20 |
| 2003/0045803 | A1 * | 3/2003 | Acharya | A61B 6/032 600/508 |
| 2003/0086535 | A1 * | 5/2003 | Teppaz | A61B 6/583 378/207 |
| 2009/0316972 | A1 * | 12/2009 | Borenstein | A61B 6/583 382/131 |
| 2011/0288406 | A1 | 11/2011 | Sosna et al. | |
| 2017/0007132 | A1 | 1/2017 | Zubkov et al. | |

OTHER PUBLICATIONS

Nickoloff, et al., "Survey of Modem Fluoroscopy Imaging:Flat-Panel Detectors versus Image Intensifiers and More", RadioGraphics 2011; 31:591-602.

PCTUS16/029237—International Search Report and Written Opinion dated Aug. 5, 2016.

Extended European Search Report, European Application No. 16786971.8, dated Jan. 10, 2019.

* cited by examiner

PHANTOMS AND METHODS AND KITS USING THE SAME

CROSS-REFERENCE TO RELATED APPLICATIONS

The present application is a 35 U.S.C. § 371 national phase application from, and claims priority to, International Application No. PCT/US2016/029237, filed Apr. 25, 2016, which claims priority under 35 U.S.C. § 119(e) to U.S. Provisional Application No. 62/152,964, filed Apr. 26, 2015, all of which applications are incorporated herein by reference in their entireties.

BACKGROUND OF THE INVENTION

Phantoms are used to calibrate imaging devices such as X-ray devices.

SUMMARY OF THE INVENTION

One aspect of the invention provides a phantom including a confined fluidic path defining a plurality of regions of monotonically decreasing, discrete cross-sectional dimensions with respect to an imaging plane.

This aspect of the invention can have a variety of embodiments. The phantom can further include one or more marker regions between adjacent regions of monotonically decreasing, discrete cross-sectional dimensions. The one or more marker regions can have a cross-sectional dimension greater than the plurality of regions. The one or more marker regions can have a cross-sectional dimension of about 625 microns.

The plurality of regions of monotonically decreasing, discrete cross-sectional dimensions can be defined by tubing of varying internal diameters. The plurality of regions of monotonically decreasing, discrete cross-sectional dimensions can be defined by a monolithic substrate.

The phantom can further include an inlet in fluidic communication with the confined fluidic path. The phantom can further include an outlet in fluidic communication with the confined fluidic path.

The phantom can be an angiographic phantom. The phantom can be an angiographic X-ray phantom.

Another aspect of the invention provides a method of assessing imaging. The method includes: placing a phantom as described herein within an imaging system; flowing one or more fluids through the phantom; and capturing one or more images of the phantom.

This aspect of the invention can have a variety of embodiments. The imaging system can be a flat-panel detector (FPD) fluoroscopy system.

Another aspect of the invention provides a kit for assessing imaging. The kit includes a phantom as described herein and instructions for use.

This aspect of the invention can have a variety of embodiments. The kit can further include a pump having sufficient strength to flow one or more fluids through the phantom.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

DEFINITIONS

The instant invention is most clearly understood with reference to the following definitions.

As used herein, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like can have the meaning ascribed to them in U.S. patent law and can mean "includes," "including," and the like.

Unless specifically stated or obvious from context, the term "or," as used herein, is understood to be inclusive.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

DETAILED DESCRIPTION OF THE INVENTION

Embodiments of the invention provide phantoms (e.g., angiographic phantoms) for use in assessing performance of various imaging modalities. Although certain embodiments of the invention are described in the context of fluoroscopy and/or X-ray angiography, embodiments of the invention are applicable to X-ray imaging, magnetic resonance imaging (MM), magnetic resonance angiography (MRA), computed tomography (CT), computed tomography angiography (CTA), fluoroscopy, vascular imaging, ultrasound vascular imaging, conventional angiography (CA), digital subtraction angiography (DSA), non-subtracted angiography, three-dimensional (3D) angiography, and the like.

Flat-Panel Detector (FPD) Fluoroscopy Systems

Flat-panel detector (FPD) fluoroscopy systems convert X-rays into a digital electronic signal. The FPD itself consists of over a million detector elements (DEL). The DEL consists of two layers: the first layer, which converts X-rays to light, and the second layer, which converts light to electrical signal. The first layer is called the scintillating layer and includes thallium-activated Cesium Iodide (CsI). The second layer includes a photodiode and a transistor. If light hits the photodiode and transistor layer, the photodiode allows electricity to be conducted; without light, the photodiode prevents the conduction of electricity. The size of the DEL determines the size of the pixel in the image produced by the FPD. For example, pixel size in a detector used for high-resolution vascular imaging is typically 154 microns.

Angiography

Angiography is a medical imaging technique that utilizes a variety of imaging modalities such as X-rays, computed tomography, magnetic resonance, and the like to visualize vessels within the human body. This includes injection of liquid contrast agents such as liquid iodine-containing agents (e.g., OMNIPAQUE® medium available from GE Healthcare of Oslo, Norway) for fluoroscopy and gadolinium-containing contrast agents for magnetic resonance angiography or ultrasound vascular contrast agents that allow for visualization of the vessels. Fluoroscopy systems are utilized by a wide variety of specialists in medicine such as interventional cardiologists, interventional radiologists, interventional neuroradiologists, interventional neurologists, and neurosurgeons. Other types of liquid radiopaque agents used to treat vascular disease processes are also injected under direct visualization using FPD fluoroscopy systems such as agents utilized to treat arteriovenous malformations of the brain, liquid embolic agents, and liquid adhesive agents.

Images obtained during contrast injections are post-processed using a digital subtraction (i.e., a mask image is subtracted from a filling image) to display only the filled vascular structure. This Digital Subtraction Angiography (DSA) technique is utilized to visualize vessels in high quality. This process of subtraction allows for visualization of the vasculature solely, without any disturbing background information from bone or soft tissue. During endovascular treatment, a similar process of subtraction is utilized for real time imaging at a lower X-ray dose, a method known as "roadmapping", where one DSA image with the highest opacification of vessels is superimposed onto a real time fluoroscopy nonsubtracted image, allowing for maneuvering through complex areas of vasculature.

During endovascular treatment of cerebrovascular lesions in the central nervous system, liquid embolic agents often must be injected under continuous fluoroscopic visualization to prevent inadvertent migration of these agents into normal vessels of the brain. This is crucial to avoid devastating clinical consequences, especially when working with arteries of the brain.

When attempting to visualize arteries of the brain, it is essential to know at what level, i.e. vessel diameter, visualization is being obtained because clinically important perforating cerebral vessels are known to have diameters as small as 120 microns and average in diameters ranging from 330 to 520 microns. Thalamoperforators may arise from the posterior cerebral artery (P1 segment), basilar artery, or superior cerebellar artery and can measure between 100 microns and 1000 microns. Thalamoperforators give off mammillary branches measuring between 120 micron and 370 micron in their outer diameter.

Embodiments of the invention provide phantoms, methods, and kits for simulating the flux of a blood arterial tree with continuous tapering that would allow assessment of modern angiographic X-ray machines, specifically their ability to test and objectify the visibility of small cerebral arteries. Such embodiments assess and improve image quality of angiographic systems, and thus increase safety of patients undergoing endovascular treatment procedures. Embodiments of the invention are particularly useful in verifying visualization capabilities at the level of about 100 microns to about 500 microns.

Phantoms

Figure 1:
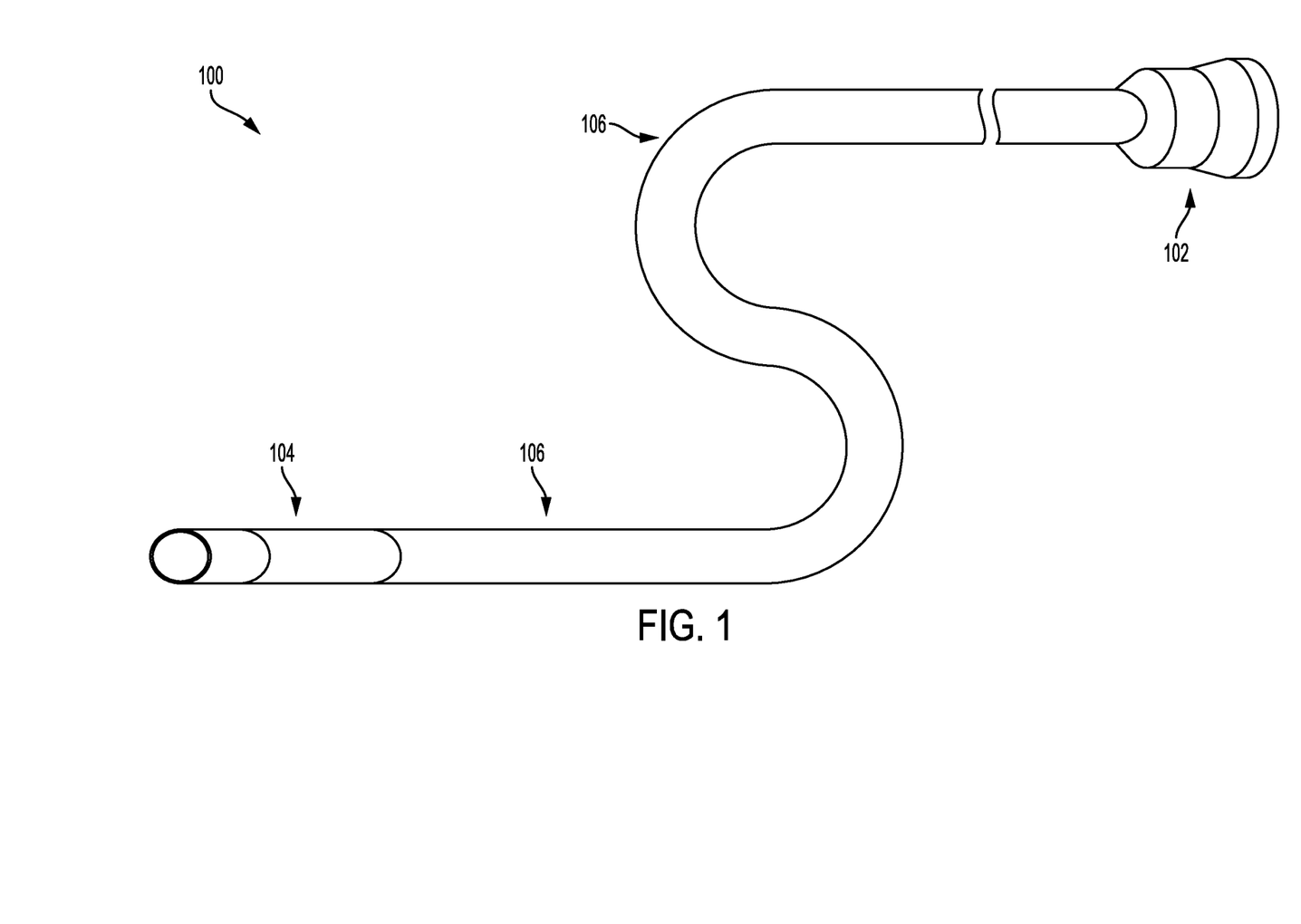
FIG. 1 depicts an phantom according to an embodiment of the invention. Flow is from the upper right to the lower left.
Figure 2A:
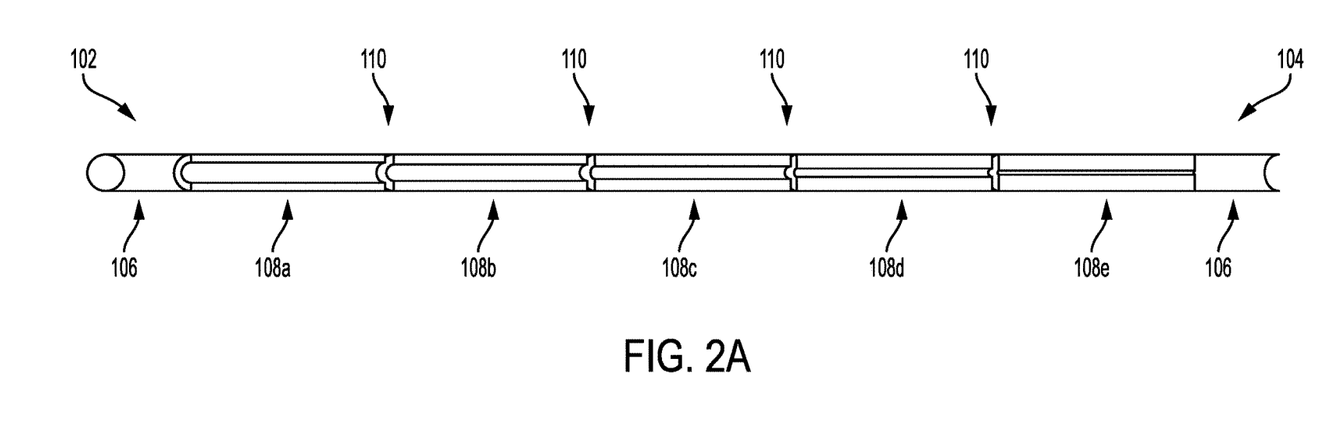
FIGS. 2A-2C provide longitudinal views of phantoms according to an embodiment of the invention. Flow is from left to right.
Figure 2B:
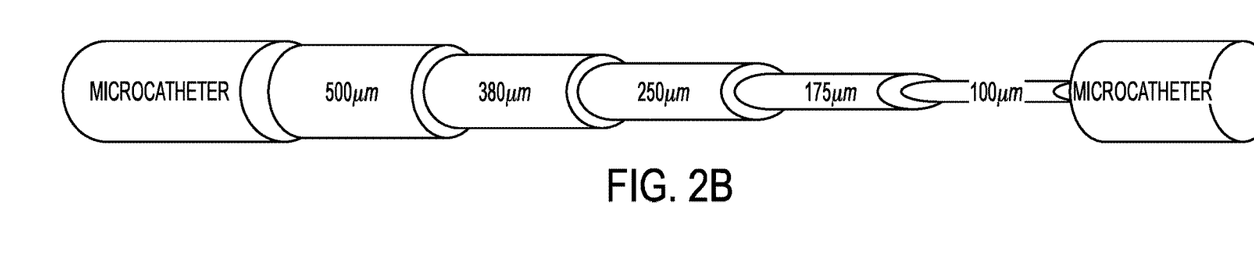
Figure 2C:
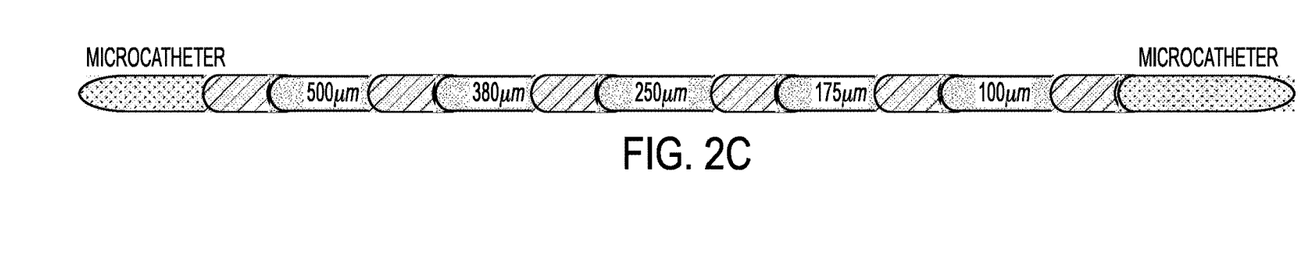

Referring now to FIG. 1, one embodiment of the invention provides a phantom 100 (e.g., an angiographic phantom). The phantom 100 includes a proximal end 102 from which fluids (e.g., liquid contrast agents) can enter and a distal end 104 from which fluids can exit. Referring now to FIG. 2A, tubing 106 can define a plurality of regions 108*a*-108*e* having various internal dimensions. In one embodiment, the tubing 106 is cylindrical and the diameters monotonically decrease (e.g., in a discrete, step-wise manner) from the proximal end 102 to the distal end 104. The outer diameter of the tubing 106 can be uniform across regions so that the thickness of the tubing 106 can vary. In other embodiments, the tubing 106 can have a substantially constant thickness and a varying outer diameter that can track the decreasing inner diameter. In either case, the tubing 106 is preferably X-ray, magnetic field, and/or radio wave transparent and should not affect imaging of the liquid contrast agents within.

In one embodiment, a single fluidic path of decreasing cross-sectional dimensions is provided. A single path may be preferred over parallel paths in order to concentrate upstream pressure to propel fluid(s) through narrower downstream regions and minimize the required pressure.

Although cylindrical fluid paths are described herein, fluid paths can have a variety of cross-sectional profiles such as rectangles, squares, and the like. In such embodiments, the relevant cross-sectional dimension would be measured in a plane parallel to the table on which the phantom sits (e.g., the bottom surface of the phantom).

Proximal end 102 can be coupled to a fluid source in order receive a liquid contrast agent. For example, the proximal end 102 can include a female Luer taper. In another example, the proximal end 102 is coupled to a motor and/or pump (e.g., a peristaltic pump) to inject a radiopaque substance. The motor and/or pump can be controllable to inject a controlled amount (e.g., by volumetric velocity and the like) of a liquid contrast agent.

FIG. 2A depicts a longitudinal 3D cross-section showing the discrete step-wise reduction in inner diameter across a plurality of regions 108*a*-108*e* as the liquid contrast agent flows from the proximal end 102 on the left to the distal end 104 on the right. Markers 110 can separate regions 106*a*-106*e*.

Markers 110 can be gaps having a sufficiently large cross-section so as to be clearly visualized in any situation and provide confirmation that the liquid contrast agent flowed through an upstream section that has a narrower cross-section. For example, markers 110 can have a cross-sectional dimension greater than the cross-sectional dimensional of a largest region 108*a*. In one embodiment, the markers 110 have a cross-sectional dimension of about 1.25 times or greater than the cross-sectional dimension of the largest region 108*a*. For example, markers 110 can have a cross-sectional dimension of about 625 microns (e.g., 1.25 times a 500 micron cross-sectional dimension of region 108a). In one embodiment, markers 110 extend perpendicular or substantially perpendicular to the regions 108.

Figure 3A:
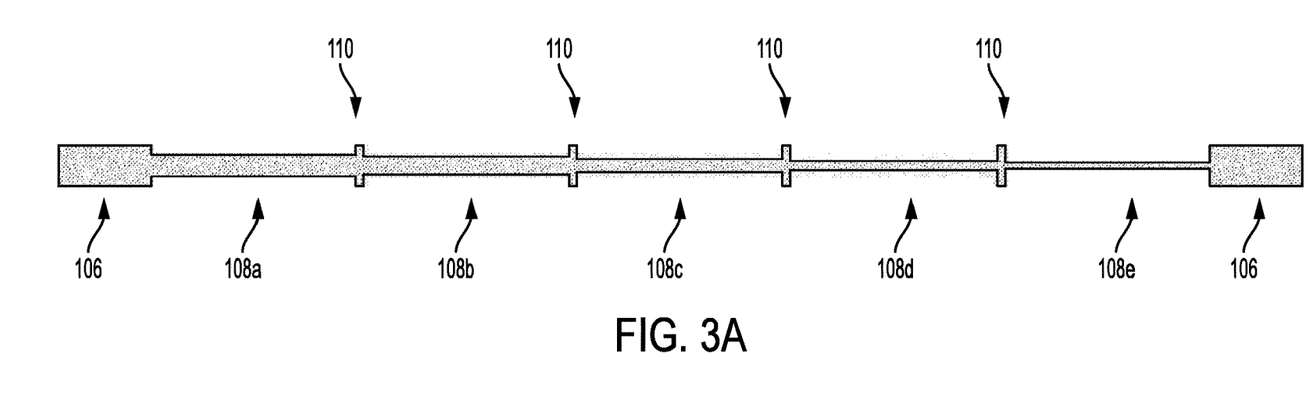
FIGS. 3A-3C depict how the model of FIG. 2A would appear during angiographic X-ray injections of contrast or other agents according to an embodiment of the invention. Flow is from left to right.
Figure 3B:
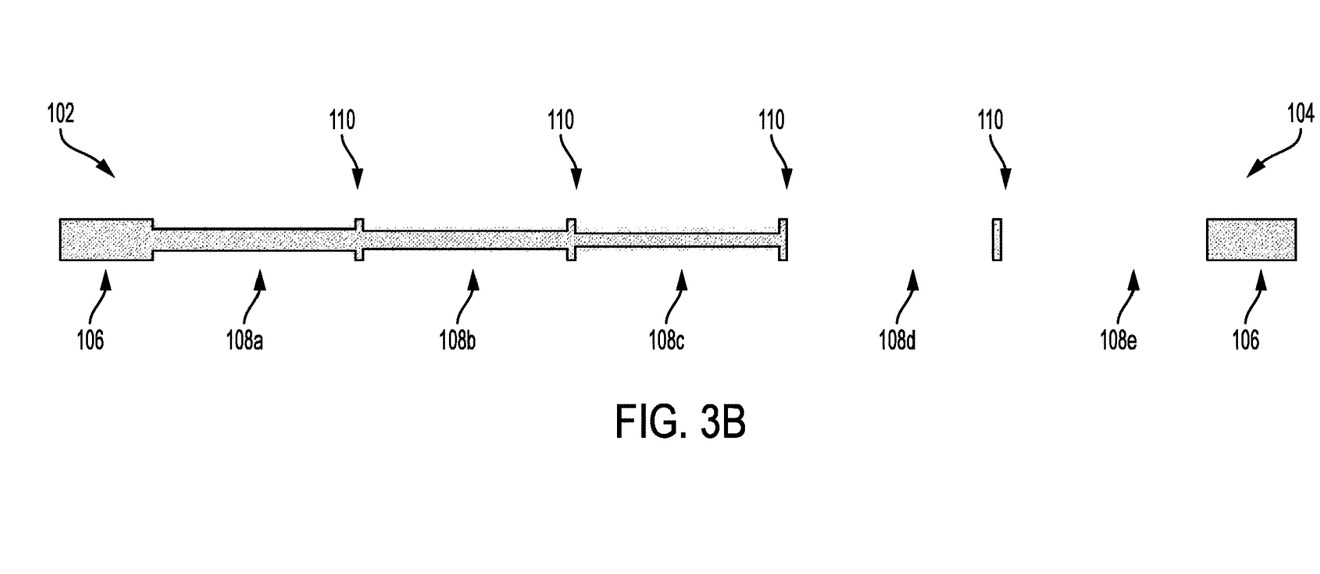
Figure 3C:
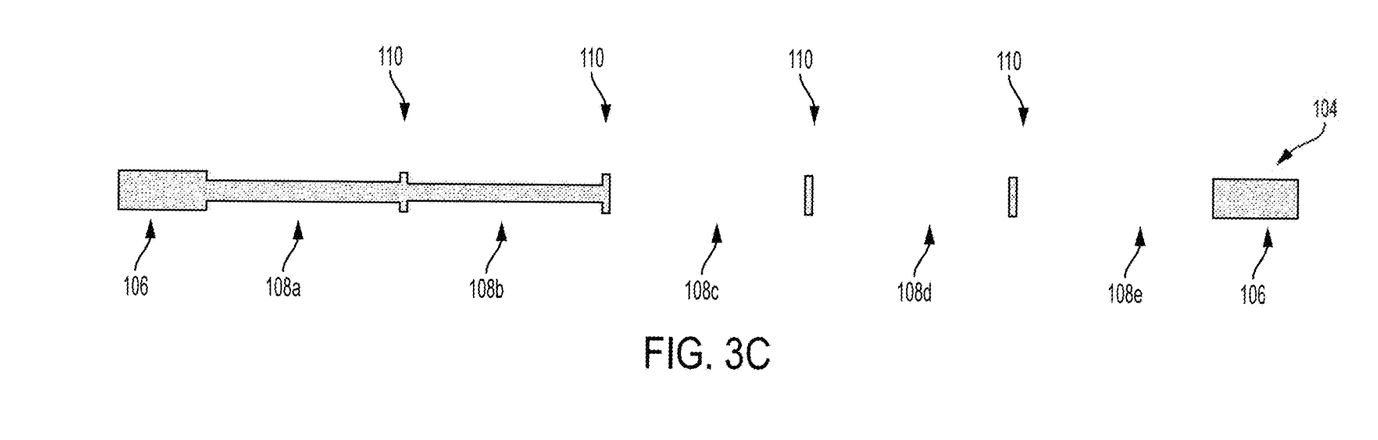

FIGS. 3A-3C depict how the model of FIG. 2A would appear during angiographic X-ray injections of contrast or other agents. The markers 110 allow for easy, quick visual identification of the different regions 108a-108e.

In FIG. 3B, the liquid contrast agent is seen filling each of markers 110 and passing through the distal end 104 on the right. However, the liquid contrast agent cannot be visualized in narrow regions 108d, 108e.

In FIG. 3C, the liquid contrast agent is seen filling each of markers 110 and passing through the distal end 104 on the right. However, the liquid contrast agent cannot be visualized in narrow regions 108c, 108d, 108e.

Figure 6A:
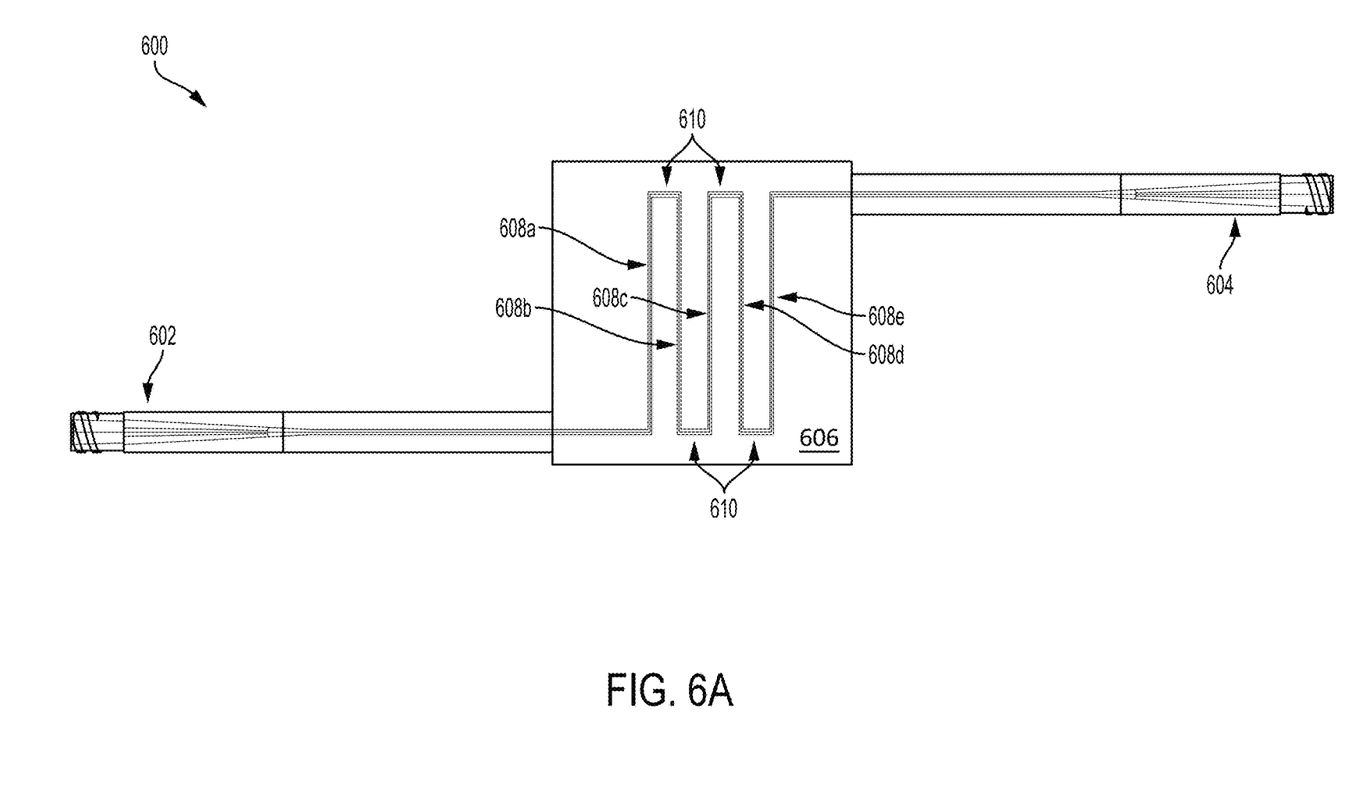
FIGS. 6A and 6B are schematics of a phantom according to an embodiment of the invention.
Figure 6B:
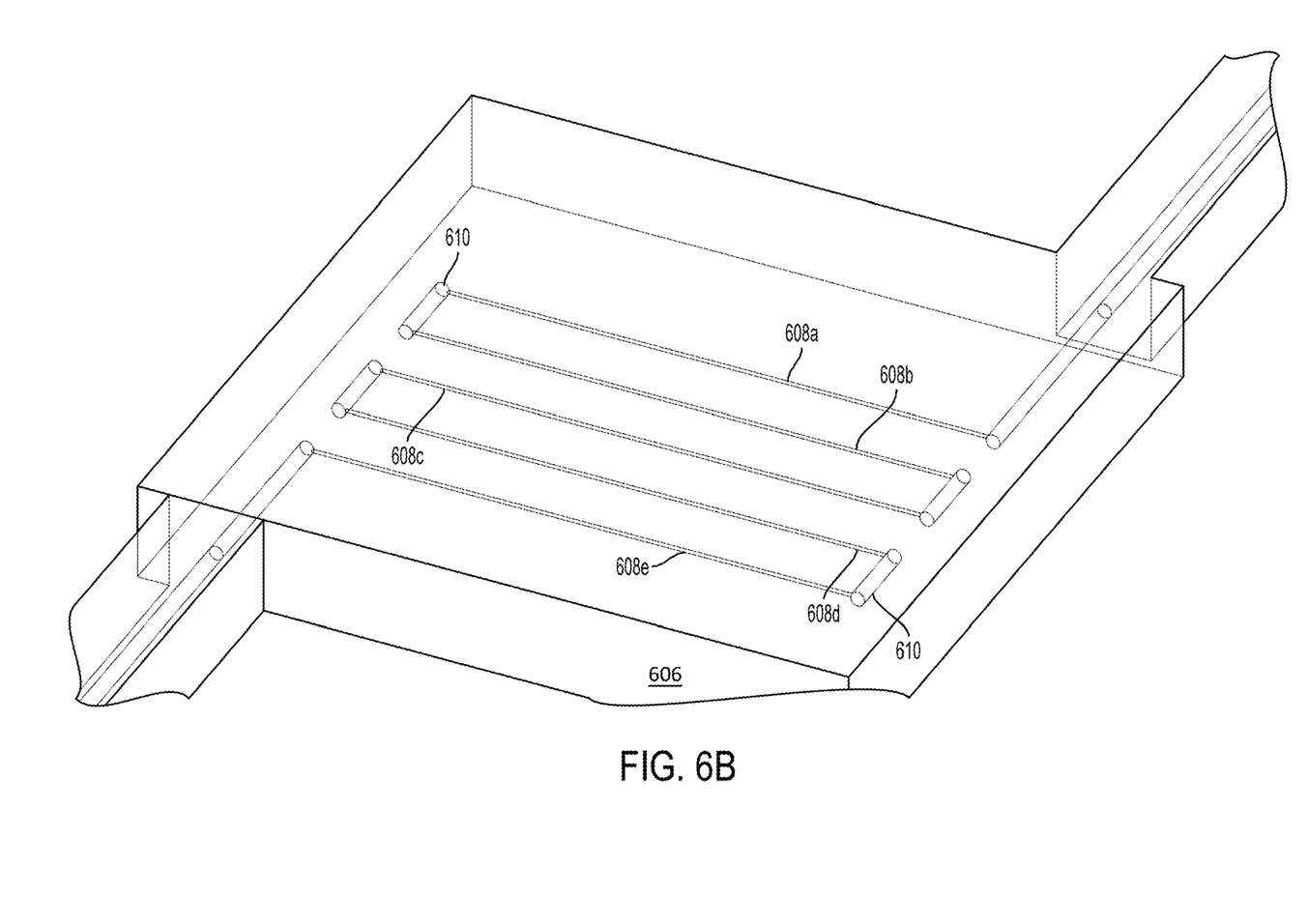

Referring now to FIGS. 6A and 6B, another embodiment of the invention provides a phantom 600 that can, for example, be fabricated from a monolithic or substantially monolithic material. Within a central region 606 between inlet 602 and outlet 604, one or more regions 608 of varying widths can be formed. In some embodiments, the regions 608a-608e and marker 610 are arranged in a serpentine pattern in which regions 608a-608e lie parallel to each other. In one embodiment, regions 608a-608e have cross-sectional dimensions (e.g., diameters) of about 500 microns, about 400 microns, about 300 microns, about 200 microns, and about 100 microns, respectively.

Sample Materials

The phantoms described herein can be fabricated from a variety of materials. In some embodiments, the phantom is includes a plurality of tubing sections. In other embodiments, the phantom includes a solid structure defining passages of varying diameter.

Phantoms are preferably fabricated from an X-ray, magnetic field, and/or radio wave transparent material. Additionally, the phantoms are preferably fabricated from a dimethyl sulfoxide (DMSO)-compatible material. Suitable materials include polymers such as LDPE, HDPE, polypropylene (PP), polypropylene copolymer (PPCO), polymethylpentene, nylon, polytetrafluoroethylene (PTFE) (e.g., TEFLON® available from The Chemours Company of Wilmington, Del.), fluorinated ethylene propylene (FEP), and the like. Other suitable materials include glass, silicon, polyetheretherketone (PEEK), other radiolucent plastics, ex vivo specimens from cadavers, and the like.

Phantoms can be fabricated using a variety of techniques including casting, molding, machining, thermomolding, thermosetting, injection molding, vacuum forming, additive manufacturing (also known as 3D printing), and the like.

Sample Liquid Contrast Agents

The phantoms and methods described herein can be utilized to assess visualization of a variety of liquid contrast agents or other contrast-containing therapeutic agents such as radiopaque iodine-containing fluids, gadolinium-containing agents, MR contrast agents, ultrasound vascular contrast agents, adhesive and non-adhesive liquid embolic agents (e.g., ONYX® available from ev3 Endovascular, Inc. of Plymouth, Minn.), acrylic glues, any substance injected under visualization during angiography, and the like.

The phantoms and methods described herein can be utilized to compare visualization of a variety of liquid contrast agents to other contrast-containing therapeutic agents.

Calibration and Comparison of Imaging Systems

The phantoms and methods described herein can be utilized to calibrate imaging devices to promote optimal imaging (e.g., of vessels having a diameter between about 120 microns and about 330 microns).

The phantoms and methods described herein can also be utilized to compare visualization of liquid contrast agents across varying imaging devices.

WORKING EXAMPLES

Figure 4:
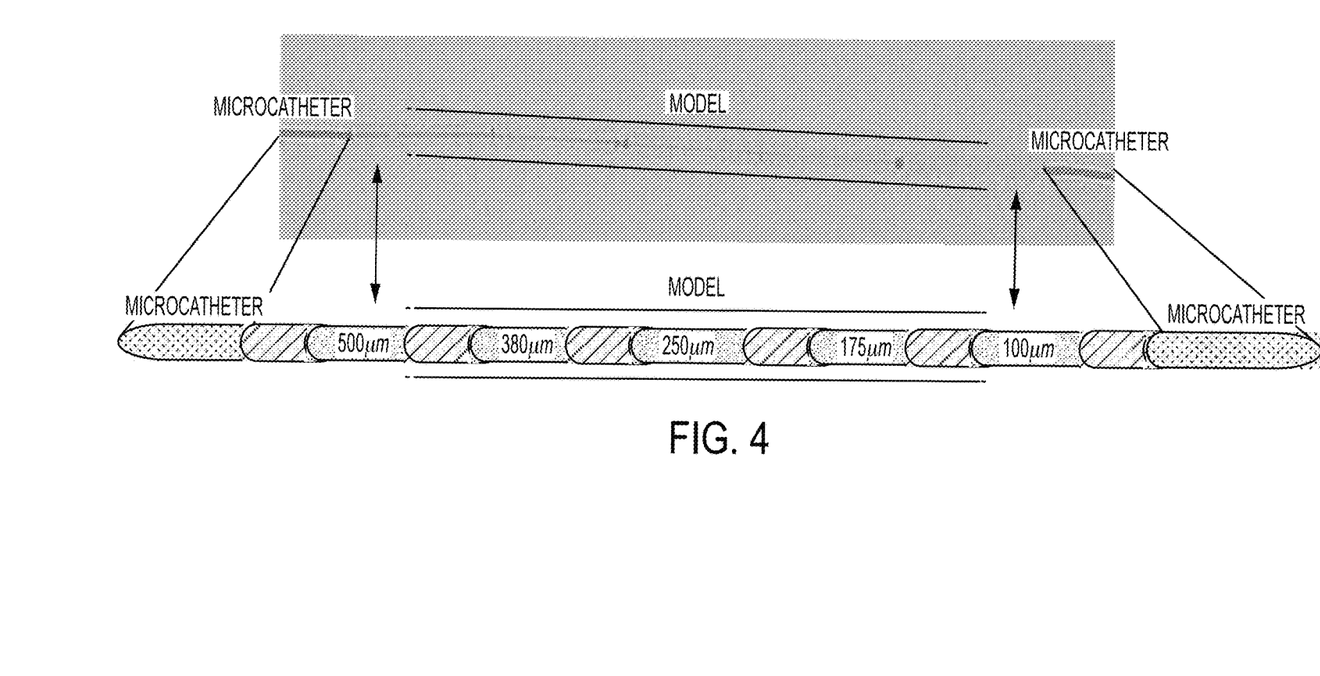
FIG. 4 overlays a schematic of a phantom according to an embodiment of the invention over an unsubtracted DSA image according to an embodiment of the invention.

Referring now to FIG. 4, a phantom prototype was imaged using a PHILIPS® ALLURA® system. Annotations show the location of the model for reference in further images.

Referring now to FIGS. 5A-5D, comparisons of visualization of standard vascular iodine contrast medium (non-diluted OMNIPAQUE® 300 medium available from GE Healthcare of Oslo, Norway) to ONYX® 18 ethylene-vinyl alcohol copolymer (EVOH), tantalum powder for radiopacity in dimethyl sulfoxide (DMSO) solvent were performed. In all figures, the contrast imaging is displayed above the ONYX® medium imaging.

Figure 5A:
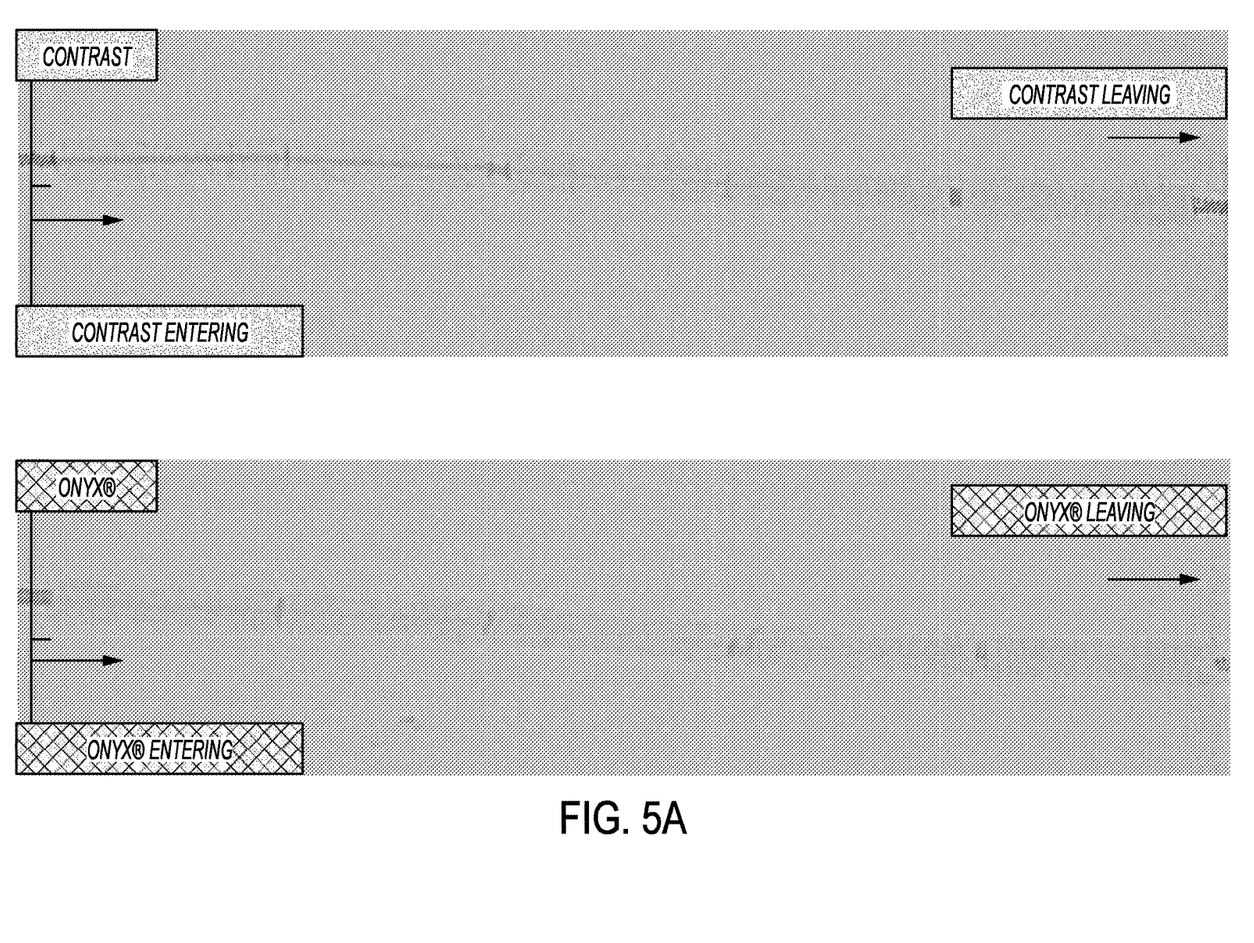
FIGS. 5A-5D depicts comparisons of visualization of standard vascular iodine contrast medium (non-diluted OMNIPAQUE® 300 medium available from GE Healthcare of Oslo, Norway) to ONYX® 18 ethylene-vinyl alcohol copolymer (EVOH), tantalum powder for radiopacity in dimethyl sulfoxide (DMSO) according to embodiments of the invention.
Figure 5B:
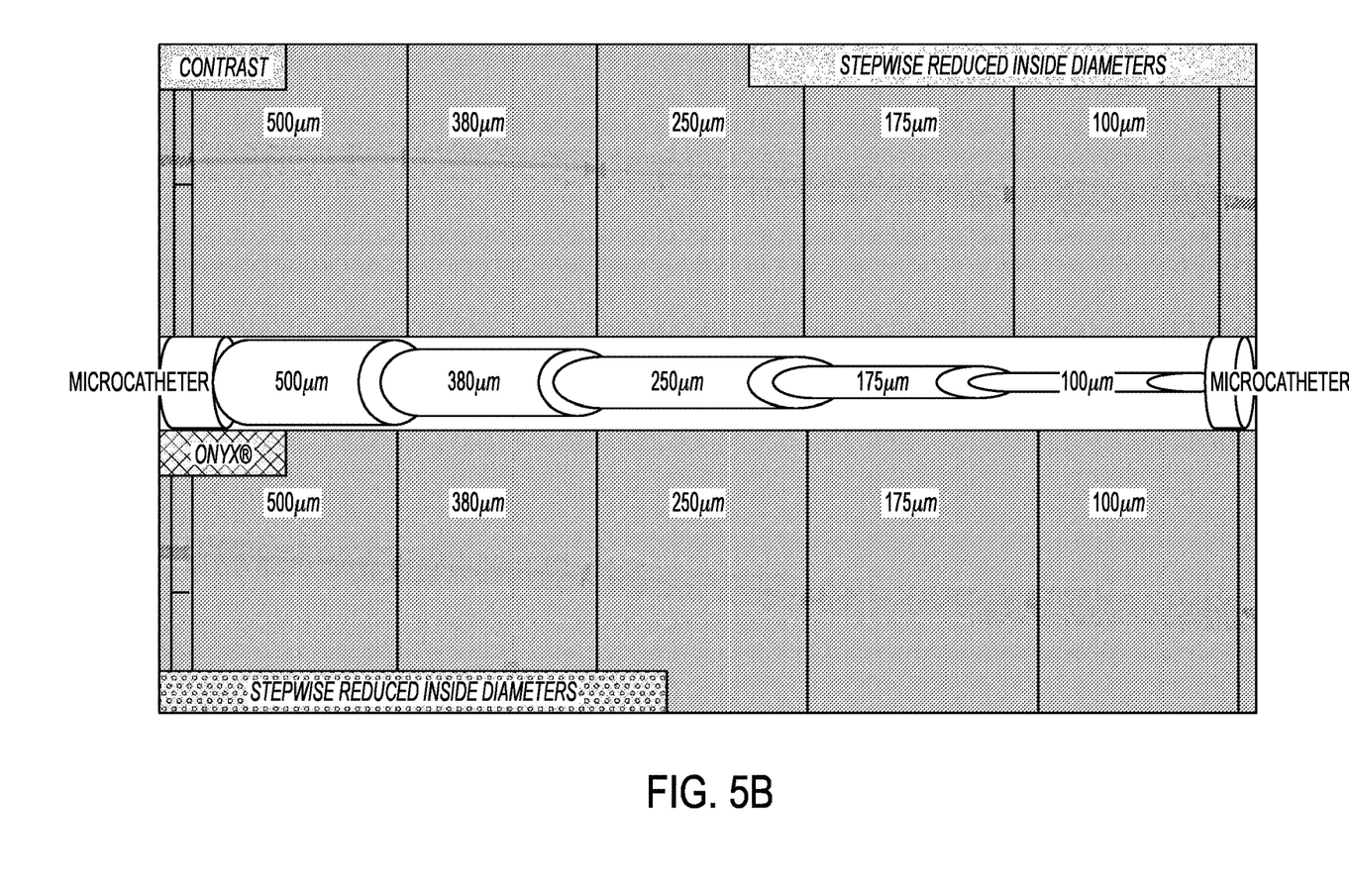

FIG. 5A provides unsubtracted DSA images in which contrast and the ONYX® medium can be seen entering and exiting the phantom. Markers are visible even when substances in adjacent segments are not visible. FIG. 5B overlays internal diameters and a schematic of the phantom. The loss of visualization of the contrast begins around 175 microns, while loss of visualization of the ONYX® medium begins around 250 microns.

Figure 5C:
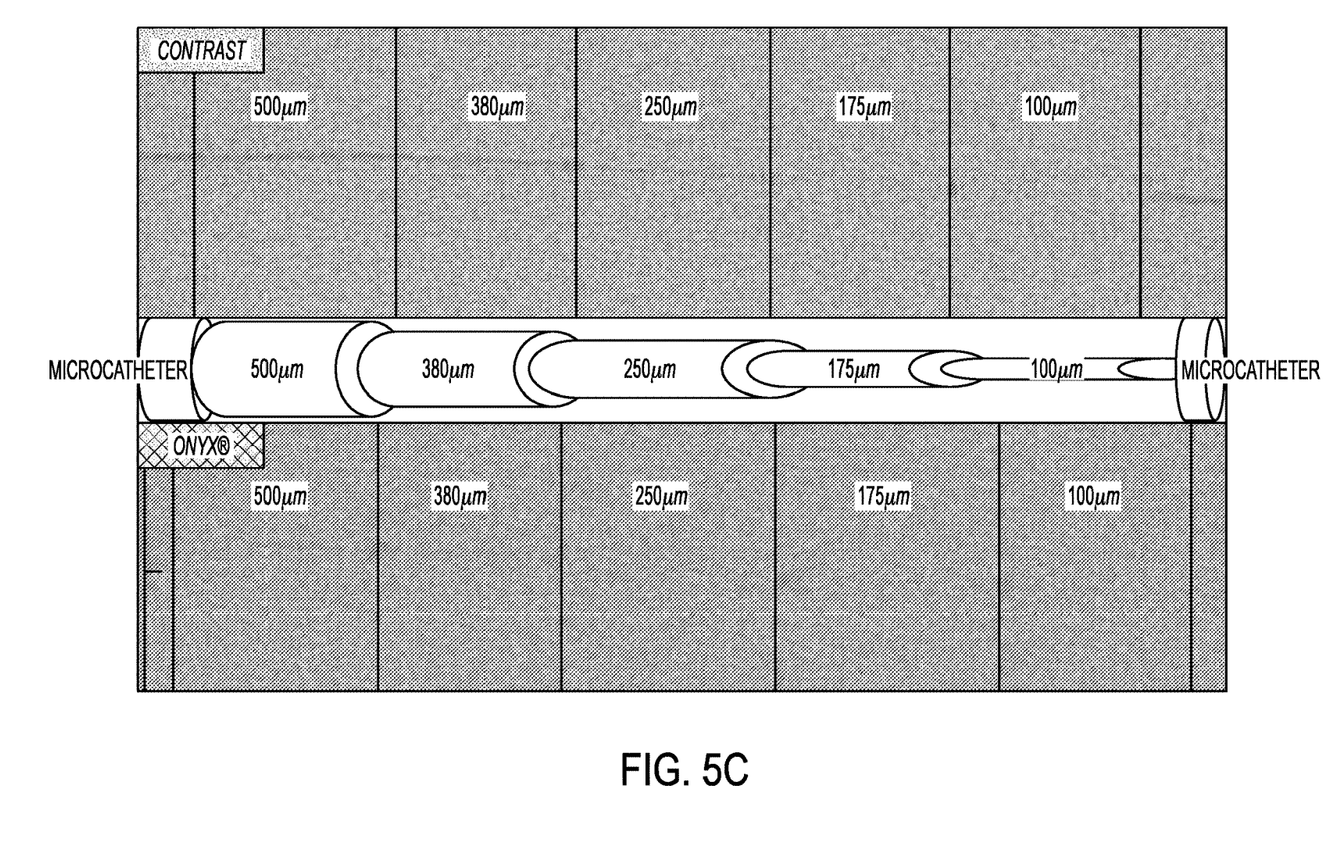
Figure 5D:
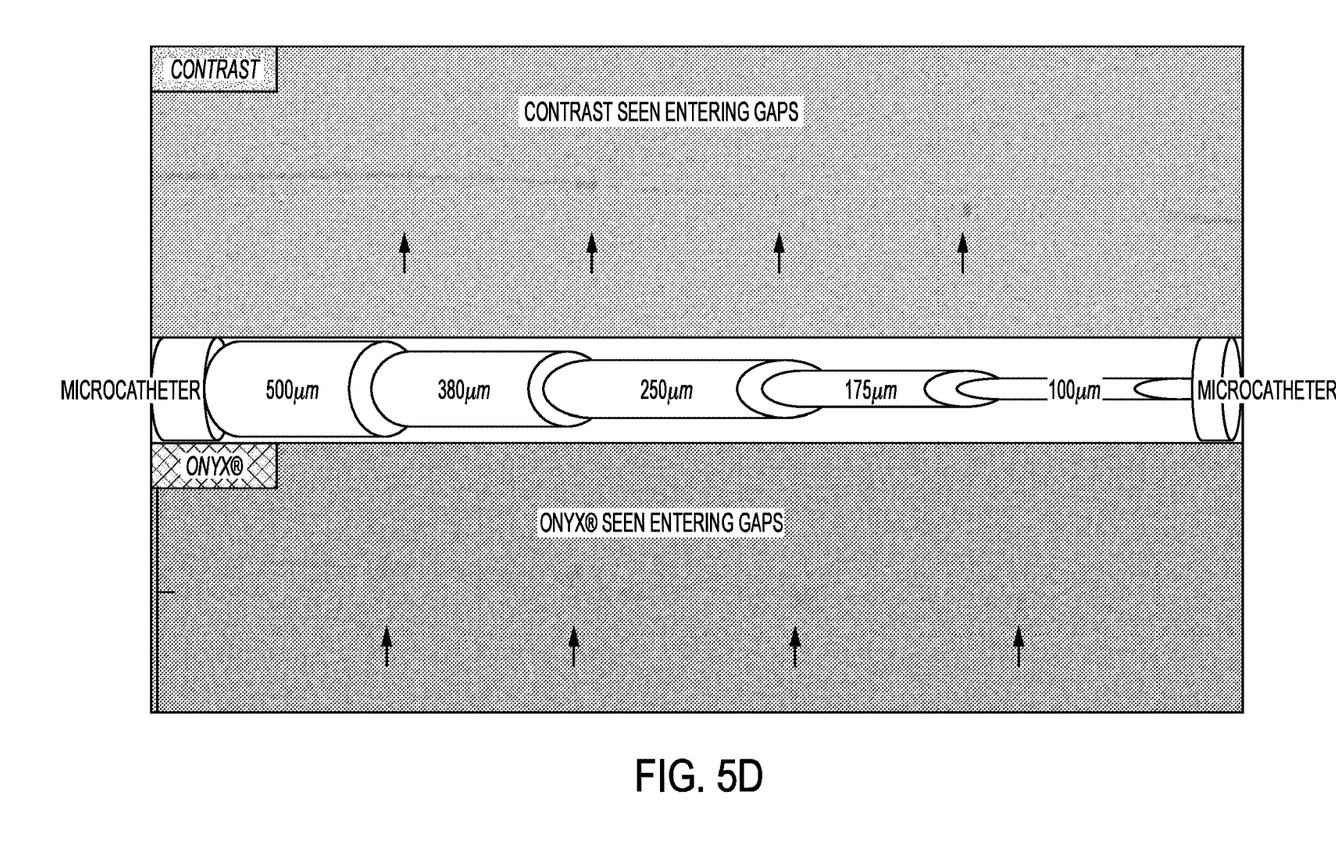

FIG. 5C provides a comparison of "roadmap" images with an overlay of the phantom. The markers remain visible as seen in FIG. 5D. The loss of visualization of the contrast begins around 250 microns, while loss of visualization of the ONYX® medium begins around 380 microns.

EQUIVALENTS

Although preferred embodiments of the invention have been described using specific terms, such description is for illustrative purposes only, and it is to be understood that changes and variations may be made without departing from the spirit or scope of the following claims.

INCORPORATION BY REFERENCE

The entire contents of all patents, published patent applications, and other references cited herein are hereby expressly incorporated herein in their entireties by reference

The invention claimed is:

1. A phantom comprising:
   a confined fluidic path defining a plurality of regions of monotonically decreasing, discrete cross-sectional dimensions with respect to an imaging plane;
   one or more marker regions between adjacent regions of monotonically decreasing, discrete cross-sectional dimensions, the one or more marker regions having a cross-sectional dimension greater than the plurality of regions.

2. The phantom of claim 1, wherein the one or more marker regions have a cross-sectional dimension of about 625 microns.

3. The phantom of claim 1, wherein the plurality of regions of monotonically decreasing, discrete cross-sectional dimensions are defined by tubing of varying internal diameters.

4. The phantom of claim 1, wherein the plurality of regions of monotonically decreasing, discrete cross-sectional dimensions are defined by a monolithic substrate.

5. The phantom of claim 1, further comprising:
an inlet in fluidic communication with the confined fluidic path.

6. The phantom of claim 5, further comprising:
an outlet in fluidic communication with the confined fluidic path.

7. The phantom of claim 1, wherein the phantom is an angiographic phantom.

8. The phantom of claim 1, wherein the phantom is an angiographic X-ray phantom.

9. A method of assessing imaging, the method comprising:
placing the phantom of claim 1 within an imaging system;
flowing one or more fluids through the phantom; and
capturing one or more images of the phantom.

10. The method of claim 9, wherein the imaging system is a flat-panel detector (FPD) fluoroscopy system.

11. A kit for assessing imaging, the kit comprising:
the phantom of claim 1; and
instructions for use.

12. The kit of claim 6, further comprising:
a pump having sufficient strength to flow one or more fluids through the phantom.

13. The phantom of claim 1, wherein the one or more marker regions extend perpendicularly from the one or more regions.

14. The phantom of claim 1, wherein the one or more marker regions are positioned between the one or more regions to form a serpentine single confined fluidic path.

15. A phantom comprising:
an inlet;
an outlet; and
a single confined fluidic path in fluidic communication with the inlet and the outlet, the single confined fluidic path comprising:
a plurality of regions of monotonically decreasing, discrete internal cross-sectional dimensions with respect to an imaging plane; and
one or more marker regions between adjacent regions of monotonically decreasing, discrete internal cross-sectional dimensions, the one or more marker regions having an internal cross-sectional dimension greater than any of the plurality of regions.

16. The phantom of claim 15, wherein the one or more marker regions extend perpendicularly from the one or more regions.

17. The phantom of claim 15, wherein the one or more marker regions are positioned between the one or more regions to form a serpentine single confined fluidic path.

* * * * *